United States Patent
Kim et al.

(10) Patent No.: US 6,414,170 B1
(45) Date of Patent: Jul. 2, 2002

(54) PREPARATION OF CATIONIC SURFACTANTS CONTAINING ESTER GROUP IN MOLECULES

(75) Inventors: Dong-Il Kim; Jeong-Wook Ha; Tae-Seong Kim; Moon-Jeong Rang, all of Daejeon (KR)

(73) Assignee: LG Chemical Ltd., Seoul (KR)

( * ) Notice: Subject to any disclaimer, the term of this patent is extended or adjusted under 35 U.S.C. 154(b) by 0 days.

(21) Appl. No.: 09/744,349

(22) PCT Filed: Jul. 27, 1999

(86) PCT No.: PCT/KR99/00407
§ 371 (c)(1),
(2), (4) Date: Jan. 23, 2001

(87) PCT Pub. No.: WO00/06679
PCT Pub. Date: Feb. 10, 2000

(30) Foreign Application Priority Data

Jul. 27, 1998 (KR) ............................................. 98-30208

(51) Int. Cl.[7] ..................... C07C 231/00; C07C 233/00; C07C 235/00; C07C 237/00; C11C 3/00
(52) U.S. Cl. ........................ 554/52; 564/291; 564/292; 564/296; 560/250
(58) Field of Search ........................... 554/52; 564/291, 564/292, 296; 560/250, 252, 222

(56) References Cited

U.S. PATENT DOCUMENTS 5,476,597 A  * 12/1995 Sakata et al. ................ 252/8.8

FOREIGN PATENT DOCUMENTS

| GB | 1386855 | 3/1975 | |
| JP | 6-199748 | 7/1994 | ......... C07C/217/28 |
| WO | WO 94/07978 | 4/1994 | ........... C11D/1/835 |

* cited by examiner

Primary Examiner—Paul J. Killos
Assistant Examiner—Zachary Tucker
(74) Attorney, Agent, or Firm—Fish & Richardson P.C.

(57) ABSTRACT

The present invention relates to a method for preparing a cationic surfactant in which physical chemical characteristics such as softness, antistatic properties, etc. as well as biodegradability are quite excellent due to having an ester group and a hydrophilic hydroxyl group in its molecules. A cationic surfactant of the present invention is prepared by reacting tertiary amine drivatives, fatty acid, and epihalohydrin, and prepared simply by reacting esterification and quaternary reactions in one step with a high yield. The above cationic surfactant is a high grade alkyl quaternary ammonium compound as represented in General Formula (1), wherein $R^1$ is a $C_1$–$C_4$ alkyl group; $R^2$ is a $C_7$–$C_{21}$ linear or branched alkyl or alkenyl group; A is $OCOR^3$, $NHCOR^3$ or OH; $R^3$ is a $C_7$–$C_{21}$ linear or branched alkyl or alkenyl group; X is a halogen atom; and n is an integral number from 2 to 6.

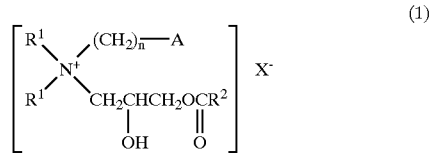

(1)

9 Claims, No Drawings

PREPARATION OF CATIONIC SURFACTANTS CONTAINING ESTER GROUP IN MOLECULES

CROSS REFERENCE TO RELATED APPLICATION

This application is based on application No. 98-30208 filed in the Korean Industrial Property Office on Jul. 27, 1998, the content of which is incorporated hereinto by reference.

BACKGROUND OF THE INVENTION a) Field of the Invention

The present invention relates to a method for preparing a cationic surfactant, and more particularly to a method for preparing a new cationic surfactant in which an esterification reaction of a fatty acid and a quaternary reaction of tertiary amine are progressed simultaneously and in a simple method so that an ester group and a hydroxyl group exist in the molecules resulting in excellent biodegradability and solubility in water.

(b) Description of the Related Art

A cationic surfactant, the hydrophilic radical portion of which is dissociated as a cation when dissolved in water, has a structure that is opposite to that of an anionic surfactant (fatty acid soap) such that it is also called an invert soap. A cationic surfactant is not only applied to produce ordinary surface activity effects such as rinsing, emulsification, solubilization, etc., but also displays softening and antistatic effects. A cationic surfactant is classified as a quaternary ammonium compound or an amine derivative depending on its structure.

Although dimethyl dialkyl ammonium chloride (DDAC) has been typically used as a representative cationic surfactant, its consumption has been decreased more and more due to the low biodegradability of DDAC. Therefore, studies related to injecting a group having a biodegradable functional group (such as ester or amide in an alkyl group) into molecules are actively being pursued.

Among the different types of cationic surfactants developed in this manner, quaternary ammonium compound of amidoamine, quaternary ammonium compound of amidoesteramine, imidazoline, and imidazoline ester based cationic surfactants are most commonly used. Examples include an amidoamine compound, and a preparing method and a softener of cationic surfactants using this compound disclosed in Japanese Patent No. Heisei 6-345704; an amidoesteramine compound, and a preparing method and a softener of cationic surfactants using this compound disclosed in Japanese Patent No. Heisei 6-336466; a softener composition containing imidazoline ester disclosed in Japanese Patent No. Heisei 4-257372; and a method for preparing a conditioning compound containing imidazoline disclosed in Japanese Patent No. Heisei 2-1479.

Nevertheless, a wide range of studies to develop cationic surfactants with excellent biodegradability are still being pursued since the biodegradability of the above patents is low despite the improvement over the biodegradability of DDAC. As a result of such research, it has been determined that if an alkyl group, which is a lipophilic part in molecules of a cationic surfactant, includes an easily degradable functional group like an ester group, its biodegradability becomes quite excellent compared with conventional dimethyl dialkyl ammonium chloride, amide based quaternary ammonium compound, and imidazoline based cationic surfactant (Tenside Surfactant Detergent, 1993, 30, 186-191).

Accordingly, various derivatives of quaternary ammonium compound having an ester group in molecules thereof are being widely studied. Typical examples, which have been commercialized, include WO 94-07978 in which a softener and a hair care product were prepared using a cationic surfactant derived from triethanol amine; WO 93/23510 in which a concentrated fabric softener and a biodegradable fabric softener composition were prepared using a cationic surfactant having ester group at two hydrophobic groups; and WO 921/5745 in which a concentrated fabric softener composition was prepared using linear fatty alcohol ethoxylate and polydialkylsiloxane, etc., in imidazoline or imidazoline ester. A concentrated fabric softening and dispersing agent comprising a quaternary ammonium compound prepared from triethanol amine and fatty acid was prepared in WO 94/14935, and a concentrated fabric softener was prepared using a small amount of a quaternary ammonium compound having an ester group in molecules (and a nonionic dispersing agent) in WO 94/13772.

However, in case of the molecules containing the above quaternary ammonium compound with an ester group, solubility in water is so low that the inherent basic properties of the quaternary ammonium compound are deteriorated when large amounts of compounds such as glycerin based, low grade alcohols and nonionic dispersing agents are used in order to maintain the long-term stability of the salt. Further, although the biodegradability of this quaternary ammonium compound has considerably been improved over the existing dimethyl dialkyl ammonium chloride (DDAC), there are still improvements required in this respect.

SUMMARY OF THE INVENTION

It is an object of the present invention to provide a method for preparing a cationic surfactant which maintains excellent softening and antistatic properties associated with quaternary ammonium compound characteristics while having a low toxicity, is and highly biodegradable as a result of having a group in its molecules, and also has excellent dispersing properties in water due to its superior solubility in water.

To achieve the above object, the present invention provides a method for preparing a cationic surfactant of the following General Formula 1 prepared by reacting tertiary amine derivatives, epihalohydrin, and fatty acids:

[General Formula 1]

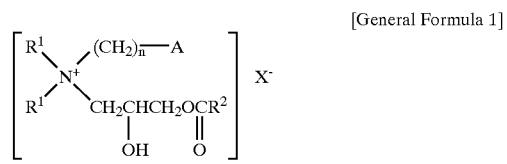

wherein $R^1$ is a $C_1$–$C_4$ alkyl group; $R^2$ is a $C_7$–$C_{21}$ linear or branched alkyl or alkenyl group; A is $OCOR^3$, $NHCOR^3$ or OH; $R^3$ is a $C_7$–$C_{21}$ linear or branched alkyl or alkenyl group; X is a halogen atom; and n is an integral number from 2 to 6.

DETAILED DESCRIPTION OF THE INVENTION

The present invention will now be described in detail. As will be realized, the invention is capable of modification in various obvious respects, all without departing from the invention. Accordingly, the description is to be regarded as illustrative in nature, and not restrictive.

The present invention is characterized in that a cationic surfactant of the following General Formula 1 is prepared by performing an esterification reaction together with a quaternary reaction without catalysts using reactants of tertiary amine derivatives, fatty acids, and epihalohydrin:

[General Formula 1]

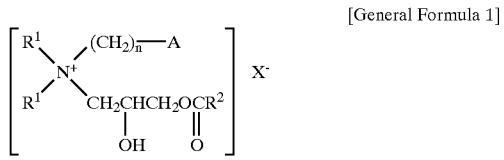

wherein $R^1$ is a $C_1$–$C_4$ alkyl group; $R^2$ is a $C_7$–$C_{21}$ linear or branched alkyl or alkenyl group; A is $OCR^3$, $NHCOR^3$ or OH; $R^3$ is $C_7$–$C_{21}$ linear or branched alkyl or alkenyl group; X is a halogen atom; and n is an integral number from 2 to 6.

A cationic surfactant of the present invention is readily biodegradable while maintaining the inherent properties of quaternary ammonium compounds, i.e., softness, antistatic properties, etc. at least equal to levels in conventional quaternary ammonium compounds, as well as containing an ester group. Furthermore, it has improved solubilities in water by employing hydrophilic parts in the molecules of the compounds.

The preparing process of this cationic surfactant is represented in the following Reaction Formula 1:

[Reaction Formula 1]

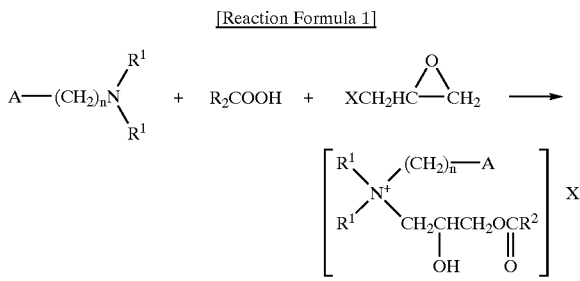

wherein $R^1$, $R^2$, A, $R^3$, X, and n are the same as in the above General Formula 1.

In the above Reaction Formula, when tertiary amine derivatives, fatty acids, and epihalohydrin are reacted simultaneously, the epihalohydrin and fatty acids are reacted to form an alkyl halide having ester group with the tertiary amine derivative acting as a catalyst. The resulting material is again reacted with tertiary amine derivative resulting in a formation of quaternary ammonium compound.

The above tertiary amine derivative is represented as in the following General Formula 2:

(General Formula 2)

wherein $R^1$ is a $C_1$–$C_4$ alkyl group; A is $OCR^3$, $NHCOR^3$ or OH; $R^3$ is a $C_7$–$C_{21}$ linear or branched alkyl or alkenyl group; and n is an integral number from 2 to 6.

The above tertiary amine derivatives are amide or tertiary amine containing ester groups which are synthesized by reacting dialkyl amino alkyl amine or dialkyl hydroxyalkyl amine derivatives with fatty acids. During the synthesis, it is preferable that the reaction temperature is 100 to 200° C., the reaction pressure is 1 to 10 atmospheres, and the reaction time is 3 to 20 hours. In case that the tertiary amine containing ester groups are prepared, a catalyst can selectively be used. The usable catalysts are phosphoric acid, hypophosphorous acid, p-toluene sulfonic acid, hydrochloric acid, etc. The consumed amount of the usable catalysts is 0.01 to 1.0 wt % of the total reactant amount.

A mixture of more than one or two fatty acids having a $C_8$–$C_{22}$ linear or branched alkyl or alkenyl group can be used as the above fatty acid. Examples include octanoic acid, decanoic acid, dodecanoic acid, tetradecanoic acid, hexadecanoic acid, octadecanoic acid, eicosanoic acid, and docosanoic acid. The fatty acids have an equivalent of 0.8 to 1.3 of tertiary amine derivatives. A drawback of the formation of an insufficient amount of the target material occurs when the consumed amount of fatty acid has an equivalent of less than 0.8 in the tertiary amine derivatives. When this equivalent is over 1.3, non-reacted fatty acid and alkyl halide having ester group remain, deteriorating physical properties.

The above epihalohydrin uses an equivalent of 1.0 to 1.3, preferably 1.0 to 1.1, in the tertiary amine derivative. The drawbacks of an increase in toxicity and a deterioration in physical properties occur as a result of the existence of non-reacted tertiary amine when the equivalent of epihalohydrin is less than 1.0 in the tertiary amine. When this equivalent is over 1.3, an insufficient amount of the target material is produced.

In a method for simultaneously reacting the above tertiary amine derivatives, epihalohydrin, and fatty acid, the reaction temperature is between 60 to 120° C. and the reaction time is from 5 to 30 hours, and a reaction solvent can be either used or not used. Examples of solvents which can be employed as reaction solvents include water, methanol, ethanol, 1-propanol, 1-butanol, 2-propanol, ethyleneglycol, glycerin, propyleneglycol, polyethyleneglycol, univalent, bivalent, trivalent, polyvalent alcohols, etc. The consumed amount of the reaction solvent is from 10 to 100 wt % of the total reactant amount.

EXAMPLES

Preferred EXAMPLES are described below to help in understanding the present invention. However, the following EXAMPLES are provided only to explain the present invention more fully, and the present invention is not restricted to the following EXAMPLES.

Example 1

Lauryl amido propyl dimethyl amine, tertiary amine containing amide group, was prepared by amidation reacting 156 g of dimethylaminopropylamine (1.53 mol, 2% excess) and 300 g of lauric acid (1.5 mol) at a temperature of 140 to 145° C. and a pressure of 3 to 4 atmospheres for 18 hours in a four-neck flask in which a mechanical agitator, thermometer, and condenser are mounted. The measured amine value was 101.6% and an acid value was 5.9%. The resulting material of the amidation reaction was then dissolved in acetone, cooled, crystallized, filtered, and dried. Next, the above prepared 100 g of laurylamidopropyidimethyl amine (0.352 mol) were placed in a reactor, following the simultaneous placing therein of 84.5 g of lauric acid (0.423 mol, 20% excess) and 39.1 g of epichlorohydrin (0.423 mol, 20% excess). Subsequently, as a solvent, 96 g of 2-propanol (30 wt % of the total reactant) were added to the reactor and reacted therein at a temperature of 90 to 95° C. for 23 hours. After the reaction, a product yield of over 95% was calculated from the remaining amine and acid content by measuring an amine value and an acid value using the Korean Standard analysis method. When this product was dissolved into acetone and then cooled, crystals were formed. The crystals were filtered and then underwent the procedure of again being dissolved in acetone, cooled, crystallized and filtered two more times. The resulting material was then dried to obtain the pure cationic surfactant of EXAMPLE 1 in a powder form. The ultimate biodegradability of this powder was evaluated.

Example 2

Using the same equipment as in EXAMPLE 1, 89 g of N,N-dimethylethanolamine (1.0 mol), 200 g of lauric acid (1.0 mol), and 92.5 g of epichlorohydrin (1.0 mol) were simultaneously put into a reactor, and then, as a solvent, 163 g of 2-propanol (30 wt % of the total reactant) were added thereto and reacted at a temperature of 70 to 80° C. for 26 hours. After the reaction, a product yield of over 95% was calculated from the remaining amine and acid content by measuring an amine value and an acid value using the Korean Standard analysis method. After the 2-propanol, which was used as a solvent, was removed from this reactant, the reactant was dissolved in ethyl ether and cooled, thereby forming crystals which were then filtered. When the solvent was removed by drying the crystals under reduced pressure, and the pure paste-type cationic surfactant of EXAMPLE 2 was obtained. The ultimate biodegradability of this paste was evaluated.

Example 3

After installing a distiller on the same equipment as used in EXAMPLE 1, N,N-dimethyllaurylesteramine, tertiary amine containing ester group, was prepared by reacting 356.6 g of N,N-dimethylethanolamine (4.0 mol, 2 equivalent) and 400 g of lauric acid (2.0 mol) at a temperature of 170 to 180° C. for 13 hours using 1.5 g of hypophosphorous acid (50% water solution) as a catalyst. At this time, water which was produced from the reaction and excess amine were removed using the distiller. The starting amine was used in subsequent reactions after it was removed by washing it twice with water after the reaction. The acid value of the above tertiary amine containing ester group, N,N-dimethyllaurylesteramine, was 0.2%. Next, the above prepared 200 g of N,N-dimethyllaurylesteramine (0.738 mol), 177 g of lauric acid (0.885 mol, 20% excess), and 81.9 g of epichlorohydrin (0.885 mol, 20% excess) were simultaneously put into a reactor using the same equipment as in EXAMPLE 1. Subsequently, 197 g of 2-propanol (30 wt % of the total reactant), used as a solvent, were added to the reactor and reacted at a temperature of 90 to 95° C. for 24 hours. After the reaction, a product yield of over 90% was calculated from the remaining amine and acid content by measuring an amine value and an acid value using the Korean Standard analysis method. After the 2-propanol, which was used as a solvent, was removed from this product, the product was dissolved in acetone and cooled, thereby forming crystals. The crystals were filtered and then underwent the procedure of again being dissolved in acetone, cooled, crystallized and filtered two more times. The resulting material was then dried to obtain the pure cationic surfactant of EXAMPLE 3 in a white powder form. The ultimate biodegradability of this powder was evaluated.

Example 4

Using the same equipment as in EXAMPLE 3, N,N-dimethylmyristylesteramine, tertiary amine containing ester group, was prepared by reacting 58.6 g of N,N-dimethylethanolamine (0.66 mol, 1.5 equivalent) and 100 g of myristic acid (0.44 mol) at a temperature of 160 to 170° C. for 15 hours using 0.3 g of hypophosphorous acid (50% water solution) as a catalyst. After the reaction, the starting amine was used in subsequent reactions after it was removed under reduced pressure. Next, the above prepared N,N-dimethylmyristylesteramine, 100 g of myristic acid (0.44 mol), and 41 g of epichlorohydrin (0.44 mol) were simultaneously put into a reactor using the same equipment as in EXAMPLE 1. Subsequently, 110 g of 2-propanol (30 wt % of the total reactant), used as a solvent, were added to the reactor and reacted at a temperature of 90 to 95° C. for 24 hours. After the reaction was finished, a product yield of over 90% was calculated from the remaining amine and acid content by measuring an amine value and an acid value using the Korean Standard analysis method. After the 2-propanol, which was used as a solvent, was removed from this product, the product was dissolved in acetone and cooled, thereby forming crystals. The crystals were filtered and then underwent the procedure of again being dissolved in acetone, cooled, crystallized and filtered two more times. The resulting material was then dried to obtain the pure cationic surfactant of EXAMPLE 4 in a white powder form. The ultimate biodegradability of this powder was evaluated.

Example 5

Using the same equipment as in EXAMPLE 3, N,N-dimethylpalmitilesteramine, tertiary amine containing ester group, was prepared by reacting 52.1 g of N,N-dimethylethanolamine (0.59 mol, 1.5 equivalent) and 100 g of palmitic acid (0.39 mol) at a temperature of 160 to 170° C. for 15 hours using 0.3 g of hypophosphorous acid (50% water solution) as a catalyst. After the reaction was finished, starting amine was used in subsequent reactions after it was removed under reduced pressure. Next, the above prepared N,N-dimethylpalmitilesteramine, 100 g of palmitic acid (0.39 mol), and 36.1 g of epichlorohydrin (0.39 mol) were simultaneously put into a reactor using the same equipment as in EXAMPLE 1. Subsequently, 110 g of 2-propanol (30 wt % of the total reactant), used as a solvent, were added to the reactor and reacted at a temperature of 90 to 95° C. for 24 hours. After the reaction was finished, a product yield of over 90% was calculated from the remaining amine and acid content by measuring an amine value and an acid value using the Korean Standard analysis method. After the 2-propanol, which was used as a solvent, was removed from this product, the product was dissolved in acetone and cooled, thereby forming crystals. The crystals were filtered and then underwent the procedure of again being dissolved in acetone, cooled, crystallized and filtered twice. The resulting material was then dried to obtain the pure cationic surfactant of EXAMPLE 5 in a white powder form. The ultimate biodegradability of this powder was evaluated.

Example 6

Using the same equipment as in EXAMPLE 3, N,N-dimethylstearylesteramine, tertiary amine containing ester group was prepared by reacting 47 g of N,N-dimethylethanolamine (0.53 mol, 1.5 equivalent) and 100 g of stearic acid (0.35 mol) at a temperature of 160 to 170° C. for 15 hours using 0.3 g of hypophosphorous acid (50% water solution) as a catalyst. After the reaction was finished, starting amine was used in subsequent reactions after it was removed under reduced pressure. Next, the above prepared N,N-dimethylstearylesteramine, 100 g of stearic acid (0.35 mol), and 32.4 g of epichlorohydrin (0.35 mol) were simultaneously put into a reactor using the same equipment as in EXAMPLE 1. Subsequently, 100 g of 2-propanol (30 wt % of the total reactant), used as a solvent, were added to a reactor and reacted at a temperature of 90 to 95° C. for 24 hours. After the reaction was finished, a product yield of over 90% was calculated from the remaining amine and acid content by measuring an amine value and an acid value using Korean Standard analysis method. After the 2-propanol, which was used as a solvent, was removed from this product, the product was dissolved in acetone and cooled, thereby forming crystals. The crystals were filtered and then underwent the procedure of again being dissolved in acetone, cooled, crystallized and filtered two more times. The resulting material was then dried to obtain the pure cationic surfactant of EXAMPLE 6 in a white powder form. The ultimate biodegradability of this powder was evaluated.

Example 7

Using the same equipment as in EXAMPLE 3, N,N-dimethylstearylesteramine, tertiary amine containing ester group, was prepared by reacting 32.6 g of N,N-dimethylethanolamine (0.37 mol, 2.0 equivalent) and 50 g of a mixed fatty acid of stearic acid and palmitic acid (0.18 mol), in which the ratio of stearic acid to palmitic acid is 7 to 3, at a temperature of 160 to 170° C. for 20 hours using 0.16 g of hypophosphorous acid (50% water solution) as a catalyst. After the reaction was finished, starting amine was used in subsequent reactions after it was removed under reduced pressure. Next, the above prepared 38.5 g of N,N-dimethylstearylesteramine (0.11 mol), 30.5 g of stearic acid (0.11 mol), and 10.35 g of epichlorohydrin (0.11 mol) were simultaneously put into a reactor using the same equipment as in EXAMPLE 1. Subsequently, 9 g of 2-propanol (10 wt % of the total reactant), used as a solvent, were added to the reactor and reacted at a temperature of 90 to 95° C. for 12 hours. After the reaction was finished, a product yield of over 90% was calculated from the remaining amine and acid content by measuring an amine value and an acid value using the Korean Standard analysis method. After the non-reacted amine was neutralized with 1.74 g of hydrochloric acid (35%), the 2-propanol, which was used as a solvent, was removed from this product, and the cationic surfactant of EXAMPLE 7 was obtained. The ultimate biodegradability of the cationic surfactant was evaluated using this.

Example 8

Using the same equipment as in EXAMPLE 1, N,N-dimethylstearylesteramine, tertiary amine containing ester group, was prepared by reflux reacting 36.6 g of N,N-dimethylethanolamine (0.41 mol) and 100 g of a mixed fatty acid of stearic acid and palmitic acid (0.37 mol), in which the ratio of stearic acid to palmitic acid is 7 to 3, at a temperature of 125 to 130° C. for 20 hours using 0.27 g of hypophosphorous acid (50% water solution) as a catalyst. 50% of the non-reacted fatty acid remained at the time when there was no longer any reaction. Next, the above prepared 45 g of N,N-dimethylstearylesteramine, 45 g of stearic acid (0.17 mol), and 35 g of epichlorohydrin (0.38 mol) were simultaneously put into a reactor. Subsequently, 25 g of 2-propanol (10 wt % of the total reactant), used as a solvent, were added to the reactor and reacted at a temperature of 90 to 95° C. for 5 hours. After the reaction was finished, a product yield of over 90% was calculated from the remaining amine and acid content by measuring an amine value and an acid value using the Korean Standard analysis method. After non-reacted amine was neutralized with 4.0 g of hydrochloric acid (35%), the 2-propanol, which was used as a solvent, was removed from this product, and the cationic surfactant of EXAMPLE 8 was obtained. The ultimate biodegradability of the cationic surfactant was evaluated.

Test Example

Evaluation of Ultimate Biodegradability

Measuring of the ultimate biodegradability was made by taking an OECD 301D Closed Bottle Test (a test for determining whether or not 60% or more can be biodegraded two weeks from the time when the sample begins decomposing during the test period of 28 days) on cationic surfactants prepared in EXAMPLES 1 to 8, dimethyl dialkyl ammonium chloride, and imidazoline ester. The results of the ultimate biodegradabilities are represented in Table 1. The ultimate biodegradabilities of cationic surfactants of EXAMPLE 1, 2, 8, and conventional cationic surfactants were less than 60%, thereby not being readily biodegradable. On the other hand, ultimate biodegradabilities of cationic surfactants of EXAMPLES 3 to 7 were more than 60%, indicating that these surfactants are readily biodegradable.

TABLE 1

| Results of ultimate biodegradability *evaluations | |
|---|---|
| EXAMPLES | Readily biodegradable |
| EXAMPLE 1 | No |
| EXAMPLE 2 | No |
| EXAMPLE 3 | Yes |
| EXAMPLE 4 | Yes |
| EXAMPLE 5 | Yes |
| EXAMPLE 6 | Yes |
| EXAMPLE 7 | Yes |
| EXAMPLE 8 | No |
| Dimethyl dialkyl ammonium chloride | No |
| Imidazoline ester ammonium salt | No |

(*Ultimate biodegradability is a test for evaluating a degree of which test samples are completely biodegraded into water and carbon dioxide)

The present invention is characterized in that a cationic surfactant with a high yield is easily obtained by reacting tertiary amine derivatives, fatty acid, and epihalohydrin in one step. A cationic surfactant, which has excellent physical chemical characteristics such as softness, antistatic properties, etc. as well as biodegradabilty due to its having an ester group and hydrophilic hydroxyl group in its molecules, can be synthesized with a high degree of purity.

While the present invention has been described in detail with reference to the preferred examples, those skilled in the art will appreciate that various modifications and substitutions can be made thereto without departing from the spirit and scope of the present invention as set forth in the appended claims.

What is claimed is:
1. A method for preparing a cationic surfactant of the following General Formula 1 cornprising the step of reacting tertiary amine derivatives, fatty acid, and epihalohydrin in the presence of a solvent:

[General Formula 1]

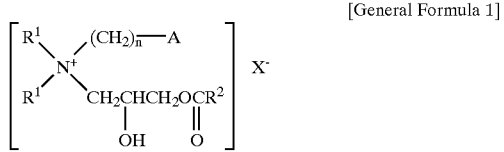

wherein $R^1$ is a $C_1$–$C_4$ alkyl group; $R^2$ is a $C_7$–$C_{21}$ linear or branched alkyl or alkenyl group; A is $OCOR^3$, $NHCOR^3$ or OH; $R^3$ is a $C_7$–$C_{21}$ linear or branched alkyl or alkenyl group; X is a halogen atom; and n is an integral number from 2 to 6.

2. A preparation method in accordance with claim 1, wherein the tertiary amine derivatives are represented in the following General Formula 2:

(General Formula 2)

wherein $R^1$ is a $C_1$–$C_4$ alkyl group; A is $OCOR^3$, $NHCOR^3$ or OH; $R^3$ is a $C_7$–$C_{21}$ linear or branched alkyl or alkenyl group; and n is an integral number from 2 to 6.

3. A preparation method in accordance with claim 1, wherein the fatty acid is a mixture comprising more than one compound having a $C_8$–$C_{22}$ linear or branched alkyl group or alkenyl group.

4. A preparation method in accordance with claim 1, wherein the tertiary amine and fatty acid are reacted in a molar ratio of 0.8–1.3:1.

5. A preparation method in accordance with claim 1, wherein the tertiary amine and epihalohydrin are reacted in a molar ratio of 1.0–1.3:1.

6. A preparation method in accordance with claim 1, wherein the reaction temperature is from 60 to 120° C.

7. A preparation method in accordance with claim 1, wherein the reaction time is from 5 to 30 hours.

8. A preparation method in accordance with claim 1, wherein the reaction solvent is selected from a group comprised of water, methanol, ethanol, 1-propanol, 1-butanol, 2-propanol, ethyleneglycol, glycerin, propyleneglycol, polyethyleneglycol, univalent, bivalent, trivalent, and polyvalent alcohols.

9. A preparation method in accordance with claim 1, wherein the solvent is from 10 to 100 wt % of total reactant amount.

* * * * *